US012491077B2

(12) United States Patent
Castro

(10) Patent No.: US 12,491,077 B2
(45) **Date of Patent: *Dec. 9, 2025**

(54) IMPLANT FOR BONE

(71) Applicant: Blue Sky Technologies, LLC, Louisville, KY (US)

(72) Inventor: Frank Castro, Louisville, KY (US)

(73) Assignee: BLUESKY TECHNOLOGIES, LLC, Louisville, KY (US)

( * ) Notice: Subject to any disclaimer, the term of this patent is extended or adjusted under 35 U.S.C. 154(b) by 348 days.

This patent is subject to a terminal disclaimer.

(21) Appl. No.: 18/108,625

(22) Filed: Feb. 12, 2023

(65) Prior Publication Data

US 2023/0190442 A1 Jun. 22, 2023

Related U.S. Application Data

(63) Continuation-in-part of application No. 16/648,518, filed as application No. PCT/US2019/054383 on Oct. 3, 2019, now Pat. No. 11,596,445.

(60) Provisional application No. 62/809,670, filed on Feb. 24, 2019.

(51) Int. Cl.
*A61F 2/44* (2006.01)
*A61F 2/02* (2006.01)

(52) U.S. Cl.
CPC . *A61F 2/44* (2013.01); *A61F 2/02* (2013.01)

(58) Field of Classification Search
CPC ............... A61F 2/4455; A61B 17/7001; A61B 17/7032; A61B 17/7034; A61B 17/7037
See application file for complete search history.

(56) References Cited

U.S. PATENT DOCUMENTS

| | | | |
|---|---|---|---|
| 3,887,186 | A | 6/1975 | Matlock, Jr. |
| 4,244,689 | A | 1/1981 | Ashman |
| 6,159,211 | A | 12/2000 | Boriani et al. |
| 6,447,525 | B2 | 9/2002 | Follmer et al. |
| 6,743,255 | B2 | 6/2004 | Ferree |
| 6,746,484 | B1 | 6/2004 | Liu et al. |
| 8,100,972 | B1 | 1/2012 | Bruffey et al. |
| 9,636,232 | B2 | 5/2017 | Neubardt |
| 9,707,100 | B2 | 7/2017 | Duffield et al. |
| 9,814,483 | B2 | 11/2017 | Vardi |
| 9,867,733 | B2 | 1/2018 | Mohan et al. |
| 2004/0078079 | A1 | 4/2004 | Foley |
| 2004/0133279 | A1 | 7/2004 | Krueger et al. |
| 2005/0119753 | A1 | 6/2005 | McGahan et al. |
| 2006/0271053 | A1 | 11/2006 | Schlapfer et al. |
| 2009/0254125 | A1 | 10/2009 | Predick |
| 2009/0265006 | A1 | 10/2009 | Seifert et al. |
| 2010/0331895 | A1 | 12/2010 | Linke |
| 2011/0098747 | A1 | 4/2011 | Donner et al. |
| 2011/0264229 | A1 | 10/2011 | Donner et al. |
| 2012/0010659 | A1 | 1/2012 | Angert et al. |
| 2012/0232599 | A1 | 9/2012 | Schoenly et al. |
| 2013/0150906 | A1 | 6/2013 | Kerboul et al. |
| 2014/0066991 | A1 | 3/2014 | Marik et al. |
| 2014/0200618 | A1 | 7/2014 | Donner |

(Continued)

FOREIGN PATENT DOCUMENTS

WO WO2001085069 11/2001

*Primary Examiner* — Ellen C Hammond
(74) *Attorney, Agent, or Firm* — BUSINESS PATENT LAW, PLLC

(57) ABSTRACT

The present invention is an implant for bone. The current implant is particularly useful in spinal surgical procedures.

20 Claims, 4 Drawing Sheets

(56) References Cited

U.S. PATENT DOCUMENTS

| | | | |
|---|---|---|---|
| 2016/0184099 | A1 | 6/2016 | Gotfried |
| 2016/0310294 | A1 | 10/2016 | McConnell et al. |

IMPLANT FOR BONE

PRIORITY

Applicant claims priority to US National Stage Application 16648518—Implant for Bone—, filed Mar. 18, 2020; that claimed priority to PCT/US2019/054383—Implant for Bone—, filed Oct. 3, 2019; that claimed the benefit of US Provisional Application No. 62/809,670—Implant for Bone—filed on Feb. 24, 2019.

BACKGROUND OF THE INVENTION

A. Field of the Invention

Among other things, the present invention is an implant for bone. The current implant is particularly suited for implantation into mammalian spinal tissues. The present implant is provided with a cutting blade. Select embodiments of the current invention include surface treatments in anticipation of improving attachment of bone to the implant.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

References that may indicate a state-of-the-art for the current invention include: 1) U.S. Pat. No. 9,814,483-Vardi discloses a method and catheter for creating an interatrial aperture; 2) U.S. Pat. No. 3,887,186-Matlock, Jr., discloses a broadhead; 3) U.S. Pat. No. 8,100,972—Bruffey, et al. discloses a spinal cage having deployable member; 4) U.S. Pat. No. 4,244,689—Ashman discloses an endosseous plastic implant; 5) US Published Patent Application 20120232599—Schoenly, et al. discloses awl screw fixation members and related systems; 6) U.S. Pat. No. 9,636,232—Neubardt discloses harvesting bone graft material for use in spinal and bone fusion surgeries; 7) US Published Patent Application 20120010659—Angert, et al. discloses a facet fusion implant; 8) U.S. Pat. No. 6,447,525—Follmer, et al. discloses apparatus and methods for removing material from a body lumen; 9) U.S. Pat. No. 9,707,100—Afferzon, et al. discloses an interbody fusion device and for implantation; 10) U.S. Pat. No. 9,707,100—Duffield discloses an interbody fusion device and system for implantation; 11) U.S. Pat. No. 9,867,733—Mohan, et al. discloses a tissue adjustment implant; 12) US Published Patent Application 20040078079—Foley discloses systems and techniques for restoring and maintaining intervertebral anatomy; 13) US Published Patent Application 20090265006—Seiftert, et al. discloses a lateral spinous process spacer; 14) US Published Patent Application 20110264229—Donner et al. discloses a sacroliliac joint fixation system; 15) US Published Patent Application 20130150906—Kerboul, et al. discloses a system and method for lockable polyaxial driver tool; 16) US Published Patent Application 20160184099—Gotfried discloses orthopedic implants; 17) US Published Patent Application 20090254125—Predick discloses a top loading polyaxial spine screw assembly with one step lockup; 18) U.S. Pat. No. 6,746,484—Liu, et al. discloses a spinal implant; 19) WO2001085069A1—Lemaire, et al discloses an anterior lumbar interbody implant; 20) U.S. Pat. No. 6,159,211—Boriani et al discloses a stackable cage system for corpectomy/vertebrectomy; 21) US Published Patent Application 20040133279A1—Krueger, et al discloses surgical implants for use as spinal spacers; 22) US Published Patent Application 20050119753A1—McGahan, et al discloses anterior impacted bone graft and driver instruments; 23) US Published Patent Application 20160310294A1—McConnell et al discloses a spinal fusion implant for oblique insertion; 24) U.S. Pat. No. 6,743,255B2—Ferree discloses a spinal fusion cage with lordosis correction; 25) US Published Patent Application 20140200618A1—Donner discloses systems and methods for fusing a sacroiliac joint and anchoring an orthopedic appliance; 26) US Published Patent Application 20060271053—Schlapfer et al. discloses fixation device for bones; 27) US Published Patent Application 20100331895—Linke discloses an osteosynthetic device; 28) US Published Patent Application 20140066991—Marik et al discloses a bone fastener and methods of use; and 29) US Published Patent Application 20110098747A1—Donner et al discloses an arcuate fixation member.

SUMMARY OF THE INVENTION

The present invention provides a biocompatible implant for bone that can be interlocked with a device distinct from the implant. The current implant is also provided with a blade for cutting tissue. Preferred embodiments of the current fastener are provided with a solid extension and blade with an aperture. The aperture can assist tissue growth, such as bone, into and through the implant as well onto the inward surfaces of the implant. Select embodiments of the implant are provided with surface treatments in anticipation of improving attachment of bone to the implant.

With regard to spinal surgical procedures, prior art traditional fixation screws fixation stability is dependent on the healthy composition of the cancellous bone. Those skilled in the art recognize the healthy cortical bone is from about 20 to about 100 times stronger than healthy cancellous bone. Those skilled in the art also know that increasing the screw length for osteoporotic bone rarely provides satisfactory resistance against the fixation screw from pulling-out or backing-out of bone. The blade of the current implant is shorter and wider than traditional fixation screws. Because of its novel structure and surgical insertion technique, the present implant has greater resistance against pulling-out or backing-out of osteoporotic bone. Further still, the blade's shorter length reduces the possibility of injury to nearby structures such as arteries, veins and nervous tissues. It is believed that the current invention's resistance to pull-out or back-out improves implant-construct stability, higher bone fusion rates and better postoperative clinical outcomes than prior art fixation screws.

For surgical procedures involving bone, the current implant can be inserted through a small linear aperture into the bone tissue. In one of the preferred uses of the current implant, subsequent to blade's surgical insertion into bone, the blade can be rotated up to 90 degrees relative to the plane of the surgical incision. Among other things, rotation of the blade increases resistance against pull-out or back-out of the blade from bone when compared to prior art fixation screws. It is also believed that the width of the implant's blade can contact a greater surface area of healthier cortical bone distinct from the surgically created cavity, thereby improving the possibility of successful postoperative bone fusion relative to prior art fixation screws.

Within the scope of the current invention, blades can be of symmetrical or asymmetrical configuration.

Symmetrical blades are typically preferred when the inner cortex is straight—a straight inner cortex as viewed from a lateral X-ray perspective looking at the spine. Asymmetrical blades are generally preferred when the inner cortex is sloped as seen on a lateral X-ray or sagittal CT scan). Regardless of whether symmetrical or asymmetrical, implants within the scope of the current invention require insertion and subsequent rotation of the blade of up to 90 degrees relative to the plane of the surgical incision.

In use, any surgical connecting rods will generally be parallel to the blades. In a first example for a laminectomy and fusion procedure, connecting rods and the present implant's blades will be generally vertical. In a second example for a laminoplasty procedure, the connecting rods and current implant's blades will be horizontal extending from the right side of the spinal elements to the left side spinal elements. The surgical incision will be up to 90 degrees offset from the final orientation of the implant's blade.

Various asymmetrical blade configurations are typically preferred when the surgical insertion corridor is not cylindrical. By way of illustration, when the current device is implanted into the posterior cervical facets, the blade is initially inserted through the posterior cortex perpendicular to the axis of the spinal cord. After insertion, the blade is rotated up to 90 degrees to be parallel to the axis of the spinal cord. It is believed that the asymmetrical blade allows for a greater surface area contact of the posterior cortex.

An aspect of the present invention is to provide an implant with a cutting blade.

Still another aspect of the present invention is to provide an implant with a blade that can be rotated up to 90 degrees relative to the surgical incision.

It is still another aspect of the present invention to provide an implant that improves resistance to pull-out or back-out and improves implant-construct stability, higher bone fusion rates and better postoperative clinical outcomes than prior art fixation screws.

Yet still another aspect of the present invention is to provide an implant with greater resistance against pulling-out or backing-out of osteoporotic bone than current fixation screws.

Still another aspect of the present invention is to provide an implant adapted for connection with a device distinct from the implant.

It is still another aspect of the present invention to provide an implant with a blade having an aperture therein.

Yet still another aspect of the present invention is to provide an implant adaptable for use in the cervical region of the spine.

Still another aspect of the present invention is to provide an implant where the blade's aperture allows a lower torsional resistance during insertion and a greater surface area for bone ingrowth or attachment of injected adhesives post implantation.

A preferred embodiment of the current invention can be described as a spinal implant adapted for interconnection with a device distinct from the spinal implant; the spinal implant comprising: a) a solid extension comprising a first end and a second end opposite the first end; b) the first end of the solid extension further comprising a polyaxial head mounted to the first end, wherein the polyaxial head is adapted for connection with the device distinct from the spinal implant; and c) a surgical blade comprising: i) an arcuate side wider than a diameter of the second end of the solid extension, wherein the solid extension extends along a longitudinal axis of the spinal implant in a direction away from the surgical blade; ii) a straight side opposite the arcuate side; the straight side of a lesser length than the arcuate side; iii) first and second converging edges connected with the arcuate side and converging toward each other as the first and second converging edges approach the straight side; and iv) an aperture proximate the center of the surgical blade; the aperture, positioned between the first and second converging edges, opening to opposed sides of a surgically created space.

Another preferred embodiment of the current invention can be described as a spinal implant adapted for interconnection with a device distinct from the spinal implant; the spinal implant comprising: a) a solid extension comprising a first end and a second end opposite the first end; b) the first end of the solid extension further comprising a polyaxial head mounted to the first end, wherein the polyaxial head is adapted for connection with the device distinct from the spinal implant; c) a surgical blade comprising: i) a slanted side relative to and wider than a diameter of the second end of the solid extension; the solid extension extending along a longitudinal axis of the spinal implant in a direction away from the surgical blade, wherein the slanted side comprises a first wing positioned on a first side of the solid extension and a second wing positioned on a second side of the solid extension; ii) a straight side opposite the slanted side; the straight side of a lesser length than the slanted side; iii) first and second converging edges connected with the slanted side and converging toward each other as the first and second converging edges approach the straight side; and iv) an aperture proximate the center of the surgical blade; the aperture, positioned between the first and second converging edges, opening to opposed sides of a surgically created space.

Still another preferred embodiment of the current invention can be described as a spinal implant adapted for interconnection with a device distinct from the spinal implant; the spinal implant comprising: a) a cylindrical extension comprising a first end and a second end opposite the first end; and b) a surgical blade comprising: i) an arcuate side wider than a diameter of the second end of the cylindrical extension, wherein the arcuate side comprises first and second opposed wings and the cylindrical extension extends away from the surgical blade along a longitudinal axis of the surgical implant; ii) a straight side opposite the arcuate side; the straight side of a lesser length than the arcuate side, wherein the longitudinal axis of the spinal implant extends though the straight side and the cylindrical extension; iii) first and second converging edges connected with the arcuate side and converging toward each other as the first and second converging edges approach the straight side; and iv) an aperture proximate the center of the surgical blade; the aperture, positioned between the first and second converging edges, opening to opposed sides of a surgically created space.

Yet another preferred embodiment of the current invention can be described as a spinal implant adapted for interconnection with a device distinct from the spinal implant; the spinal implant comprising: a) a cylindrical extension comprising a first end and a second end opposite the first end; and b) a surgical blade comprising: i) a slanted side relative to and wider than a diameter of the second end of the cylindrical extension and connected to the second end of the cylindrical extension, wherein the slanted side comprises a first wing positioned on a first side of the cylindrical extension and a second wing positioned on a second side of the cylindrical extension; ii) a straight side opposite the slanted side; the straight side of a lesser length than the slanted side, wherein a longitudinal axis of the cylindrical extension extends through the straight side; iii) first and second converging edges connected with the slanted side and converging toward each other as the first and second converging edges approach the straight side; and iv) an aperture proximate the center of the surgical blade; the aperture, positioned between the first and second converging edges, opening to opposed sides of a surgically created space.

It is the novel and unique interaction of these simple elements which creates the apparatus and methods, within the ambit of the present invention. Descriptions of preferred embodiments of the invention follow. However, it is to be understood that the best mode descriptions do not limit the scope of the present invention.

DESCRIPTION OF THE PREFERRED EMBODIMENTS

Figure 1:
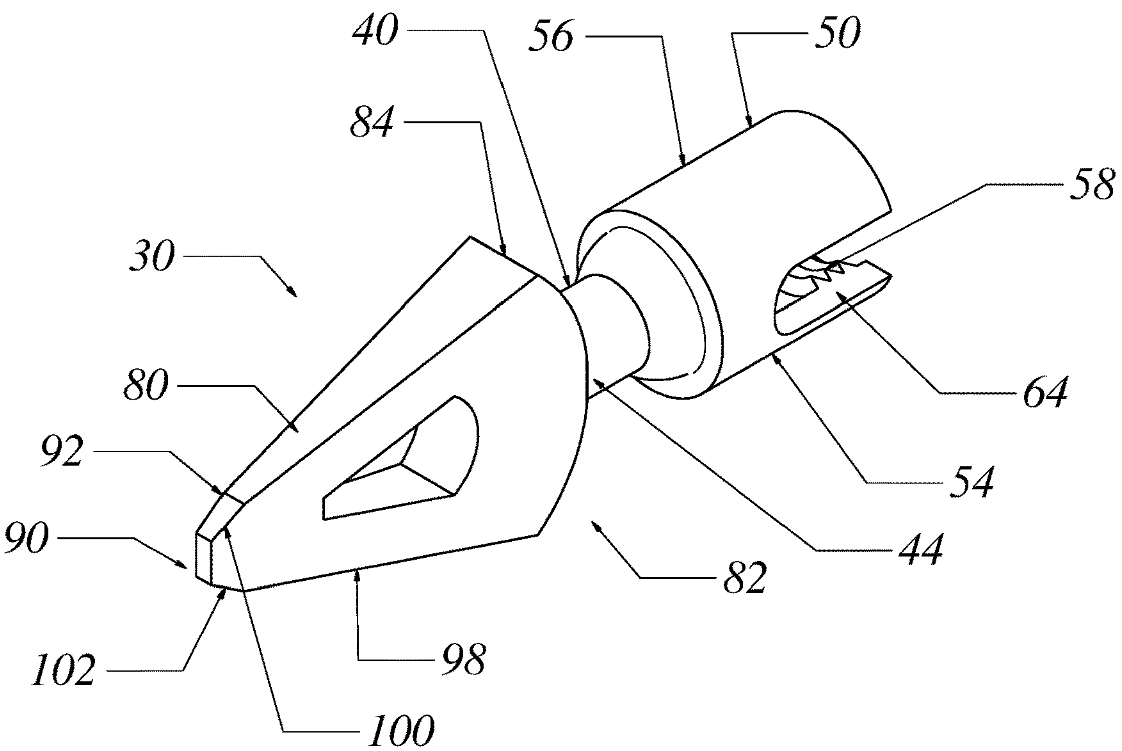
FIG. 1 is a perspective of a first preferred embodiment of the implant.

Although the disclosure hereof is detailed to enable those skilled in the art to practice the invention, the embodiments published herein merely exemplify the present invention.

In the most general sense, the present invention is an implant for bone where the implant is adapted for connection with a device distinct from the implant. Among other things, the current invention can be adapted for use with vertebra or other bone tissues. The present implant is particularly adapted for use in the cervical region of the spine. Dispersion of adhesives from the windows or openings of the surgical incision before closing the surgical wound, reduces the risk of the fastener backing out of the wound prior to the fastener fully interlocking with tissue overgrowth. Polymethymethacrylate is an adhesive particularly well suited for use with the current fastener.

Preferred embodiments of the present invention are manufactured of titanium alloys, stainless steel, non-resorbable polymers or any other composition acceptable in the art. Within the scope of the present invention, it has advantageously been discovered that cylindrical extension (40) can have lengths from about 2 to about 10 millimeters; polyaxial heads (50) can have lengths of from about 5 millimeters to about 25 millimeters; sockets (54) of polyaxial heads (50) can have depths from about 3 millimeters to about 23 millimeters, diameters from about 4 millimeters to about 20 millimeters, lateral openings widths (62, 64) from about 3 millimeters to about 10 millimeters; and blades (80, 120) can have lengths of from about 3 millimeters to about 12 millimeters, widths of from about 4 millimeters to about 10 millimeters and heights of from about 0.2 millimeters to about 4 millimeters.

Figure 2:
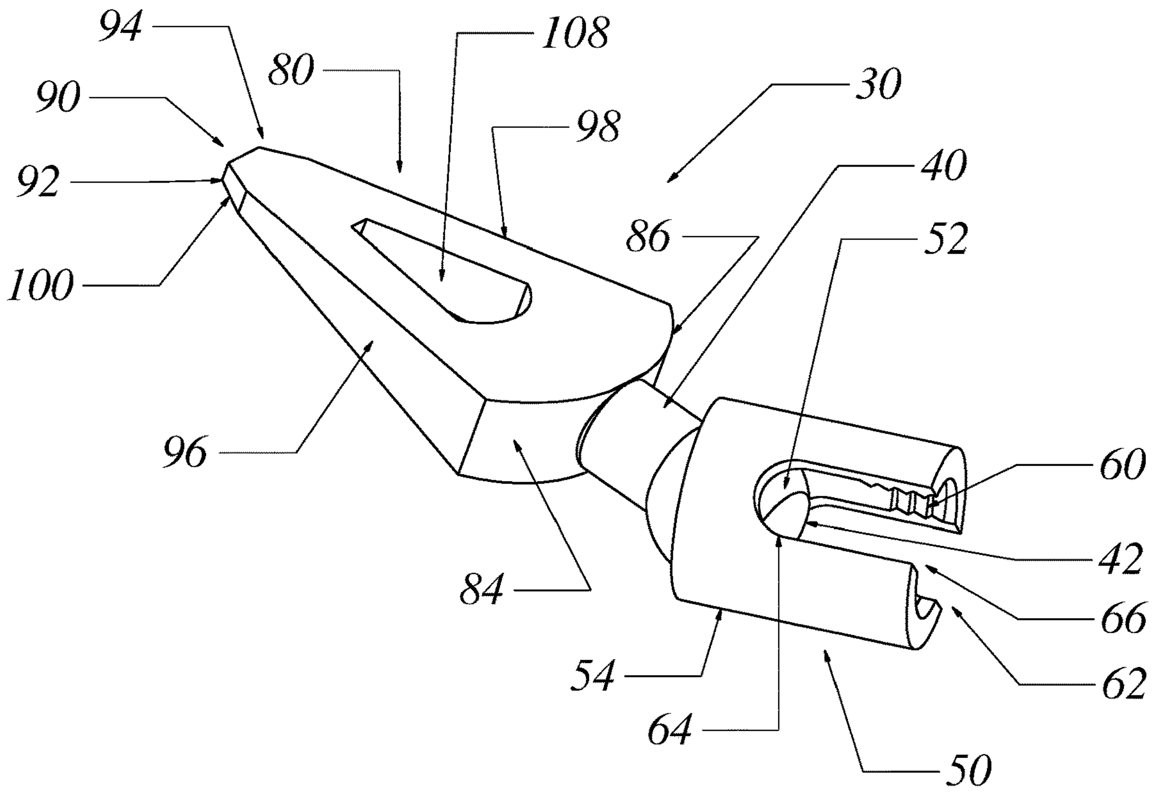
FIG. 2 is a perspective of a first preferred embodiment of the implant.

FIGS. 1 and 2 are perspectives of a first preferred embodiment of implant (30). Within the scope of the current invention, implant (30) can be interconnected with a device distinct from the implant. It has been discovered that implant (30) is useful for spinal surgeries, and, in particular, surgeries for the cervical region of the spine.

Among other things, the preferred embodiment of implant (30), enabled in FIGS. 1 and 2, includes cylindrical extension (40), polyaxial head (50) and blade (80). Cylindrical extension (40) includes first end (42) and second end (44). Select preferred embodiments of cylindrical extension (40) and blade (80) create a uniform solid implant (30). Although not shown in the drawings, when engineering parameters require, extension (40) can be of geometric configurations other than cylindrical.

Polyaxial head (50) of implant (30) is adapted for connection with a device (not shown) distinct from implant (30). Examples of devices connectable to polyaxial head (40) include but are not limited to: rods, bars, cross-links, screws and locking nuts. Polyaxial head (50) is provided with spheroid (52) connected to first end (42) of cylindrical extension (40) and socket (54) connected to spheroid (52). Prior to surgical fixation, the combination of spheroid (52) and socket (54) allows polyaxial head (50) to be moved in a multitude of axes relative to cylindrical extension (40). Socket (54) is provided with an outward housing (56) and inward receptacle (58) including one or more threads (60). Selected preferred embodiments of housing (56) can be provided with openings (62, 64, 66) adapted to receive one or more devices distinct from implant (30).

Cylindrical extension (40) extends away from arcuate side (82) of blade (80). Arcuate side (82) of blade (80) is of a dimension wider than the diameter of cylindrical extension (40). Arcuate side (82) includes first wing (84) and second wing (86) where each wing (84, 86) extends away from the longitudinal axis of cylindrical extension (40). As shown in FIGS. 1 and 2, each wing (84, 86) is arched away from first end (42) of cylindrical extension (40).

Straight side (90) of blade (80) is of lesser length than arcuate side (82) and positioned opposite from arcuate side (82). Straight side (90) includes first end (92) and second end (94). First converging edge (96) connected to first wing (84) and second converging edge (98) connected second wing (86) converge toward each other as the converging edges (96, 98) approach straight side (90). Select preferred embodiments of the current invention can be provided with first transitional edge (100) connected to first end (92) of straight side (90) and first converging edge (96) and second transitional edge (102) second end (94) of straight side (90) and converging edge (98). Within the scope of the current invention, select preferred embodiments of implant (30) are not provided with transitional edges (100, 102) and converging edges (96, 98) are connected directly to first end (92, 94) of straight side (90). Regarding the current implant (30), straight side (90), converging edges (96, 98) and transitional edges (100, 102) are adapted to surgically cut bone and other tissues.

Implant (30) is provided with aperture (108) proximate the center of blade (80) that opens to a surgically created space. Aperture (108), among other things, allows a lower torsional resistance during insertion and a greater surface area for bone ingrowth or attachment of injected adhesives post implantation.

Figure 3:
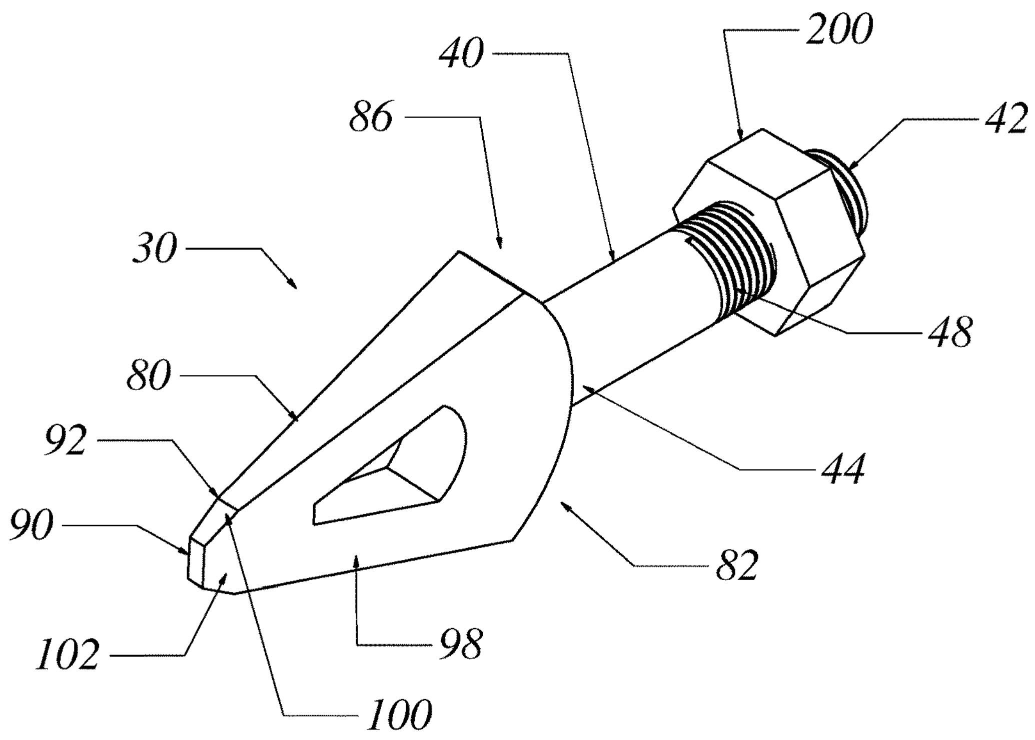
FIG. 3 is a perspective of a second preferred embodiment of the implant.
Figure 4:
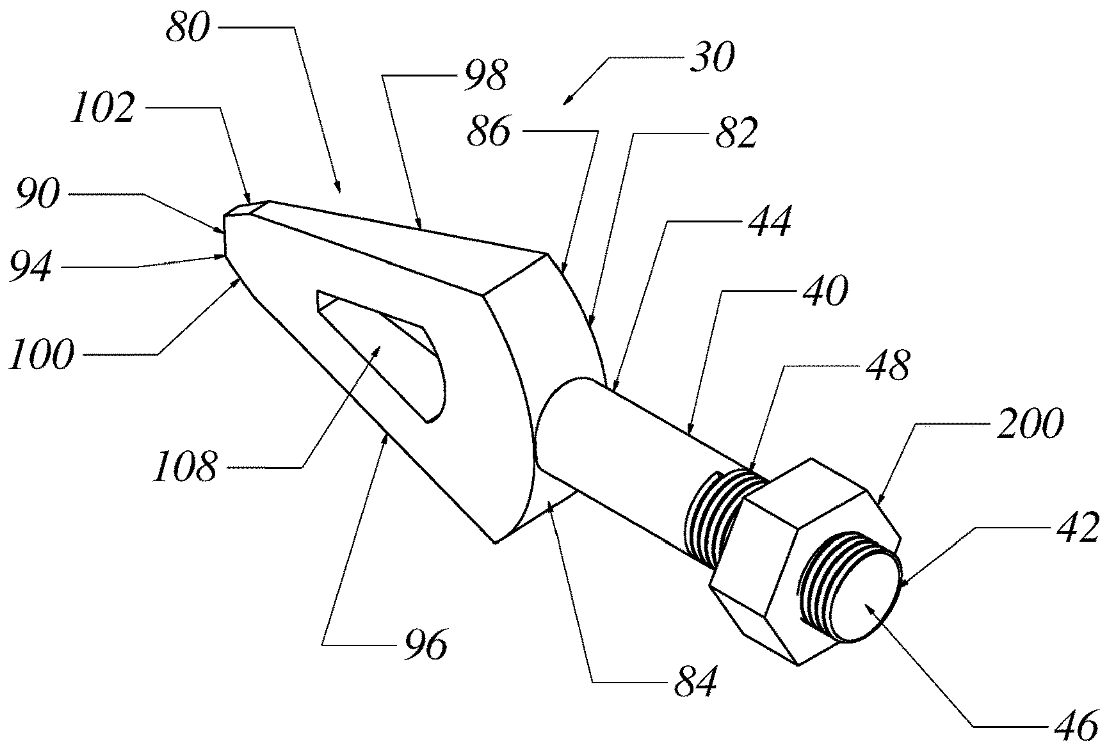
FIG. 4 is a perspective of a second preferred embodiment of the implant.

FIGS. 3 and 4 are perspectives of a second preferred embodiment of implant (30). Within the scope of the current invention, implant (30) can be interconnected with a device distinct from the implant, such as a nut (200) or other device (not shown) for coupling with implant (30). It has been discovered that implant (30) is useful for spinal surgeries, and, in particular, surgeries for the cervical region of the spine.

Among other things, the preferred embodiment of implant (30), enabled in FIGS. 3 and 4, includes cylindrical extension (40) and blade (80). Cylindrical extension (40) includes first end (42) and second end (44). First end (42) of cylindrical extension (40) is provided with thread (48) that can be utilized to connect implant (30) to a device distinct from implant (30). Thread (48) runs about at least a portion of the outward side of cylindrical extension (40) and advances from first end (42) toward the second end (44) of cylindrical extension (40). Preferred embodiments of cylindrical extension (40) are solid. Select preferred embodiments of cylindrical extension (40) and blade (80) create a uniform solid implant (30). Although not shown in the drawings, when engineering parameters require, extension (40) can be of geometric configurations other than cylindrical.

Cylindrical extension (40) extends away from arcuate side (82) of blade (80). Arcuate side (82) of blade (80) is of a dimension wider than the diameter of cylindrical extension (40). Arcuate side (82) is also provided with first wing (84) and second wing (86) where each wing (84, 86) extends away from the longitudinal axis of cylindrical extension (40). As shown in FIGS. 3 and 4, each wing (84, 86) is arched away from first end (42) of cylindrical extension (40).

Straight side (90) of blade (80) is of lesser length than arcuate side (82) and positioned opposite from arcuate side (82). Straight side (90) includes first end (92) and second end (94). First converging edge (96) connected to first wing (84) and second converging edge (98) connected second wing (86) converge toward each other as the converging edges (96, 98) approach straight side (90). Select preferred embodiments of the current invention can be provided with first transitional edge (100) connected to first end (92) of straight side (90) and first converging edge (96) and second transitional edge (102) second end (94) of straight side (90) and converging edge (98). Within the scope of the current invention, select preferred embodiments of implant (30) are not provided with transitional edges (100, 102) and converging edges (96, 98) are connected directly to first end (92, 94) of straight side (90). Regarding the current implant (30), straight side (90), converging edges (96, 98) and transitional edges (100, 102) are adapted to surgically cut bone and other tissues.

Implant (30) is provided with aperture (108) proximate the center of blade (80) that opens to a surgically created space. Aperture (108), among other things, allows a lower torsional resistance during insertion and a greater surface area for bone ingrowth or attachment of injected adhesives post implantation.

Figure 5:
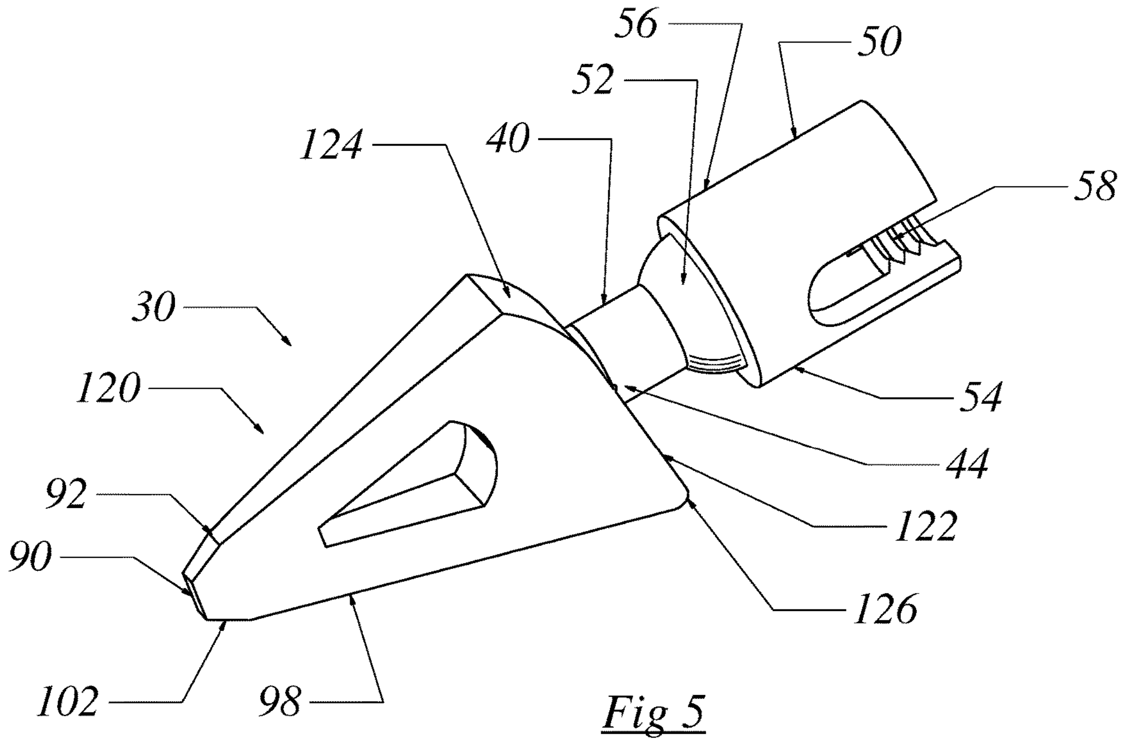
FIG. 5 is a perspective of a third preferred embodiment of the implant.
Figure 6:
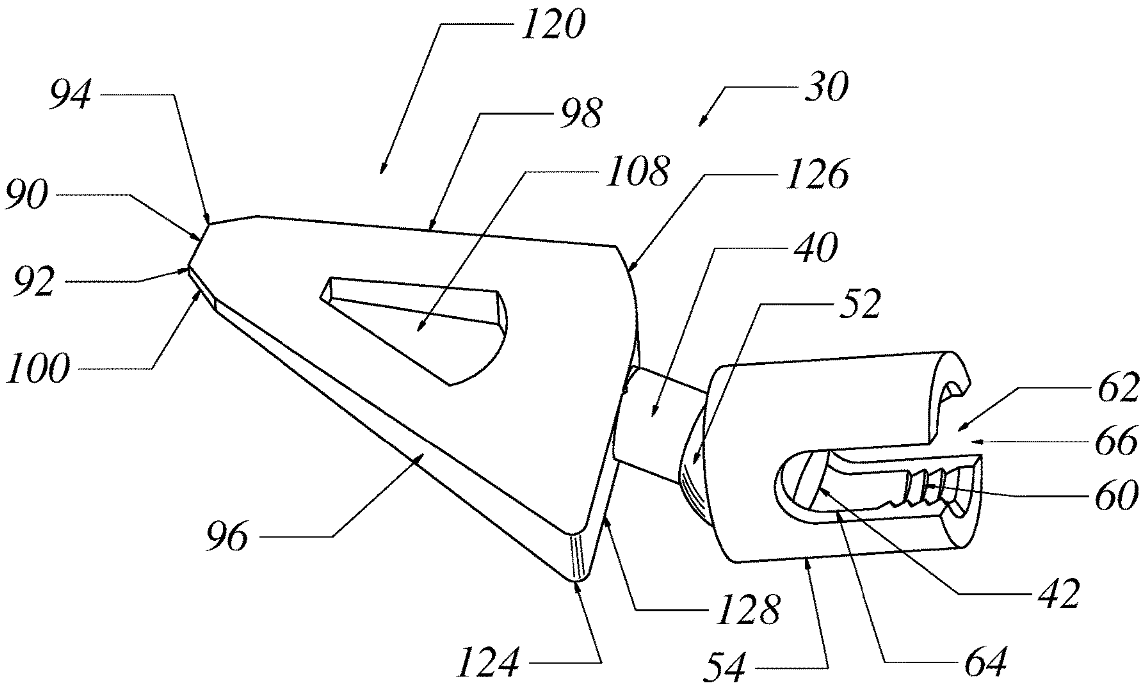
FIG. 6 is a perspective of a third preferred embodiment of the implant.

FIGS. 5 and 6 are perspectives of a third preferred embodiment of implant (30). Within the scope of the current invention, implant (30) can be interconnected with a device distinct from the implant. It has been discovered that implant (30) is useful for spinal surgeries, and, in particular, surgeries for the cervical region of the spine.

Among other things, the preferred embodiment of implant (30), enabled in FIGS. 5 and 6, includes cylindrical extension (40), polyaxial head (50) and blade (120). Cylindrical extension (40) is a solid and includes first end (42) and second end (44). Select preferred embodiments of cylindrical extension (40) and blade (80) create a uniform solid implant (30). Although not shown in the drawings, when engineering parameters require, extension (40) can be of geometric configurations other than cylindrical.

Polyaxial head (50) of implant (30) is adapted for connection with a device (not shown) distinct from implant (30). Examples of devices connectable to polyaxial head (50) include but are not limited to: rods, cross-links, bars, screws, and locking nuts. Polyaxial head (50) is provided with spheroid (52) connected to first end (42) of cylindrical extension (40) and socket (54) connected to spheroid (52). Prior to surgical fixation, the combination of spheroid (52) and socket (54) allows polyaxial head (50) to be moved in a multitude of axes relative to the longitudinal axis of cylindrical extension (40). Socket (54) is provided with an outward housing (56) and inward receptacle (58) including one or more threads (60). Selected preferred embodiments of housing (56) can be provided with openings (62, 64, 66) adapted to receive one or more devices distinct from implant (30).

Slanted side (122) of blade (120) is connected with second side (44) of cylindrical extension (40). Slanted side (122) of blade (120) is of a dimension wider than the diameter of cylindrical extension (40). Slanted side (122) includes first wing (124) and second wing (126) where each wing (124, 126) extends away from the longitudinal axis of cylindrical extension (40). As shown in FIGS. 5 and 6, a first one of the wings (124, 126) is arcuate and arched away from the first end cylindrical extension (40). A second one of the wings (124, 126) is provided with a pitched plane (128) facing first end (42) of cylindrical extension (40). The combination of an arcuate wing and a wing including a pitched plane creates an asymmetric blade (120). Pitched plane (128) intersects the longitudinal axis of implant (30) at an angle of between five and eighty five degrees as measured from the distal point of pitched plane (128) to the intersection of pitched plane and implant's (30) longitudinal axis.

Straight side (90) of blade (120) is of lesser length than slanted side (122) and positioned opposite from slanted side (122). Straight side (90) includes first end (92) and second end (94). First converging edge (96) connected to first wing (124) and second converging edge (98) connected second wing (126) converge toward each other as the converging edges (96, 98) approach straight side (90). Select preferred embodiments of the current invention can be provided with first transitional edge (100) connected to first end (92) of straight side (90) and first converging edge (96) and second transitional edge (102) second end (94) of straight side (90) and converging edge (98). Within the scope of the current invention, select preferred embodiments of implant (30) are not provided with transitional edges (100, 102) and converging edges (96, 98) are connected directly to first end (92, 94) of straight side (90). Regarding the current implant (30), straight side (90), converging edges (96, 98) and transitional edges (100, 102) are adapted to surgically cut bone and other tissues.

Implant (30) is provided with aperture (108) proximate the center of blade (80) that opens to a surgically created space. Aperture (108), among other things, allows a lower torsional resistance during insertion and a greater surface area for bone ingrowth or attachment of injected adhesives post implantation.

Figure 7:
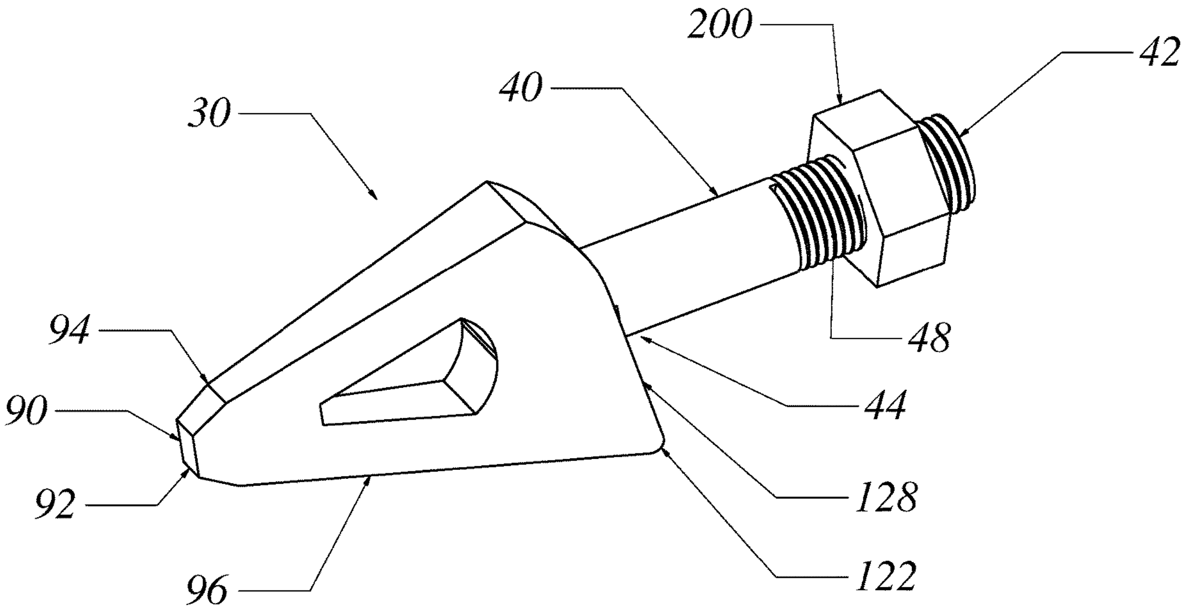
FIG. 7 is a perspective of a fourth preferred embodiment of the implant.
Figure 8:
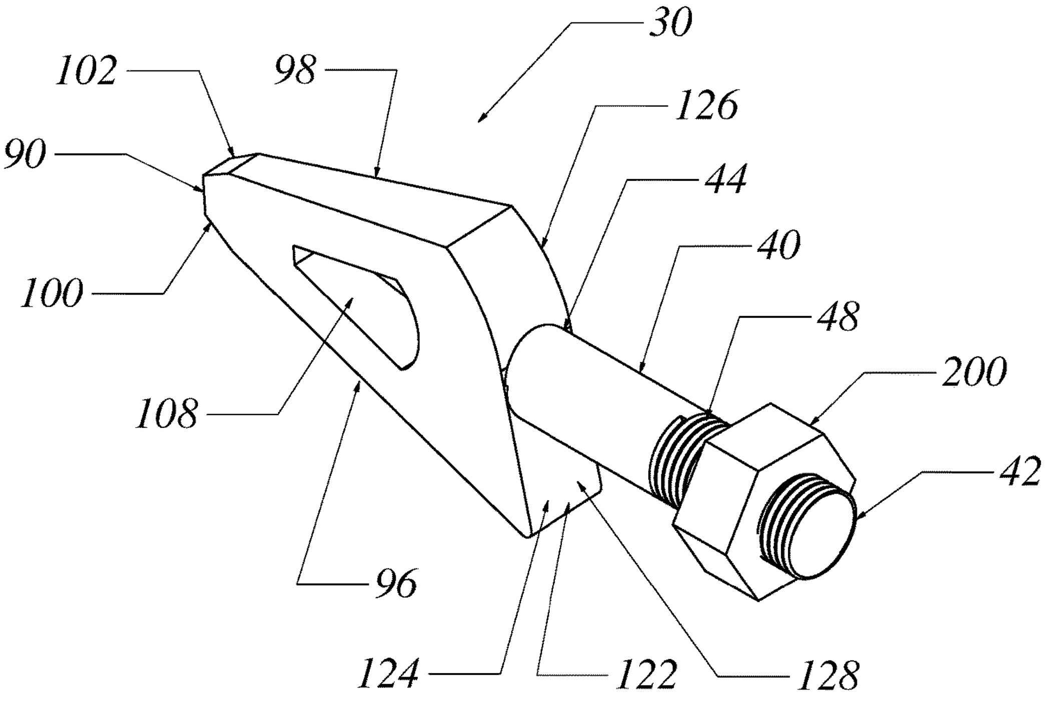
FIG. 8 is a perspective of a fourth preferred embodiment of the implant.

FIGS. 7 and 8 are perspectives of a fourth preferred embodiment of implant (30). Within the scope of the current invention, implant (30) can be interconnected with a device distinct from the implant, such as a nut (200) or other device (not shown) for coupling with implant (30). It has been discovered that implant (30) is useful for spinal surgeries, and, in particular, surgeries for the cervical region of the spine.

Among other things, the preferred embodiment of implant (30), enabled in FIGS. 7 and 8, includes cylindrical extension (40) and blade (120). Cylindrical extension (40) is a solid and includes first end (42) and second end (44). Select preferred embodiments of cylindrical extension (40) and blade (80) create a uniform solid implant (30). Although not shown in the drawings, when engineering parameters require, extension (40) can be of geometric configurations other than cylindrical.

First end (42) of cylindrical extension (40) is provided with thread (48) that can be utilized to connect implant (30) to a device distinct from implant (30). Thread (48) runs about at least a portion of the outward side of cylindrical extension (40) and advances from first end (42) toward the second end (44) of cylindrical extension (40).

Slanted side (122) of blade (120) is connected with second side (44) of cylindrical extension (40). Slanted side (122) of blade (120) is of a dimension wider than the diameter of cylindrical extension (40). Slanted side (122) includes first wing (124) and second wing (126) where each wing (124, 126) extends away from the longitudinal axis of cylindrical extension (40). As shown in FIGS. 7 and 8, a first one of the wings (124, 126) is arcuate and arched away from the first end cylindrical extension (40). A second one of the wings (124, 126) is provided with a pitched plane (128) facing first end (42) of cylindrical extension (40). The combination of an arcuate wing and a wing including a pitched plane creates an asymmetric blade (120). Pitched plane (128) intersects the longitudinal axis of implant (30) at an angle of between five and eighty five degrees as measured from the distal point of pitched plane (128) to the intersection of pitched plane and implant's (30) longitudinal axis.

Straight side (90) of blade (120) is of lesser length than slanted side (122) and positioned opposite from slanted side (122). Straight side (90) includes first end (92) and second end (94). First converging edge (96) connected to first wing (124) and second converging edge (98) connected second wing (126) converge toward each other as the converging edges (96, 98) approach straight side (90). Select preferred embodiments of the current invention can be provided with first transitional edge (100) connected to first end (92) of straight side (90) and first converging edge (96) and second transitional edge (102) second end (94) of straight side (90) and converging edge (98). Within the scope of the current invention, select preferred embodiments of implant (30) are not provided with transitional edges (100, 102) and converging edges (96, 98) are connected directly to first end (92, 94) of straight side (90). Regarding the current implant (30), straight side (90), converging edges (96, 98) and transitional edges (100, 102) are adapted to surgically cut bone and other tissues.

Implant (30) is provided with aperture (108) proximate the center of blade (80) that opens to a surgically created space. Aperture (108), among other things, allows a lower torsional resistance during insertion and a greater surface area for bone ingrowth or attachment of injected adhesives post implantation.

Applicant has enabled, described and disclosed the invention as required by the Patent Cooperation Treaty and Title 35 of the United States Code.

What is claimed is:

1. A spinal implant adapted for interconnection with a device distinct from the spinal implant; the spinal implant comprising:

a) a solid extension comprising a first end and a second end opposite the first end;

b) the first end of the solid extension further comprising a polyaxial head mounted to the first end, wherein the polyaxial head is adapted for connection with the device distinct from the spinal implant; and c) a surgical blade comprising:

i) an arcuate side wider than a diameter of the second end of the solid extension, wherein the solid extension extends along a longitudinal axis of the spinal implant in a direction away from the surgical blade;

ii) a straight side opposite the arcuate side; the straight side of a lesser length than the arcuate side;

iii) first and second converging edges connected with the arcuate side and converging toward each other as the first and second converging edges approach the straight side; and iv) an aperture proximate the center of the surgical blade; the aperture, positioned between the first and second converging edges, opening to opposed sides of a surgically created space.

2. The spinal implant of claim 1, wherein the surgical blade and the solid extension are uniform and a first wing and a second wing are arched away from the first end of the solid extension.

3. The spinal implant of claim 2, wherein the polyaxial head comprises an outer housing and a threaded inward receptacle adapted to receive the device distinct from the spinal implant.

4. The spinal implant of claim 3, comprising a first transition edge connected to the first converging edge and the straight side and a second transition edge connected to the second converging edge and the straight side.

5. A spinal implant adapted for interconnection with a device distinct from the spinal implant; the spinal implant comprising:

a) a solid extension comprising a first end and a second end opposite the first end;

b) the first end of the solid extension further comprising a polyaxial head mounted to the first end, wherein the polyaxial head is adapted for connection with the device distinct from the spinal implant;

c) a surgical blade comprising:

i) a slanted side relative to and wider than a diameter of the second end of the solid extension; the solid extension extending along a longitudinal axis of the spinal implant in a direction away from the surgical blade, wherein the slanted side comprises a first wing positioned on a first side of the solid extension and a second wing positioned on a second side of the solid extension;

ii) a straight side opposite the slanted side; the straight side of a lesser length than the slanted side;

iii) first and second converging edges connected with the slanted side and converging toward each other as the first and second converging edges approach the straight side; and iv) an aperture proximate the center of the surgical blade; the aperture, positioned between the first and second converging edges, opening to opposed sides of a surgically created space.

6. The spinal implant of claim 5, wherein the surgical blade and the solid extension are uniform.

7. The spinal implant of claim 6, wherein the slanted side intersects with the longitudinal axis of the solid extension at angles other than perpendicular.

8. The spinal implant of claim 7, wherein either the first wing or the second wing is arcuate.

9. The spinal implant of claim 8, wherein the polyaxial head comprises an outer housing and a threaded inward receptacle adapted to receive the device distinct from the spinal implant.

10. The spinal implant of claim 9 comprising a first transition edge connected to the first converging edge and the straight side and a second transition edge connected to the second converging edge and the straight side.

11. A spinal implant adapted for interconnection with a device distinct from the spinal implant; the spinal implant comprising:

a) a cylindrical extension comprising a first end and a second end opposite the first end; and b) a surgical blade comprising:

i) an arcuate side wider than a diameter of the second end of the cylindrical extension, wherein the arcuate side comprises first and second opposed wings and the cylindrical extension extends away from the surgical blade along a longitudinal axis of the surgical implant;

ii) a straight side opposite the arcuate side; the straight side of a lesser length than the arcuate side, wherein the longitudinal axis of the spinal implant extends though the straight side and the cylindrical extension;

iii) first and second converging edges connected with the arcuate side and converging toward each other as the first and second converging edges approach the straight side; and iv) an aperture proximate the center of the surgical blade; the aperture, positioned between the first and second converging edges, opening to opposed sides of a surgically created space.

12. The spinal implant of claim 11, wherein the surgical blade and the cylindrical extension are uniform and the first wing and the second wing are arched away from the first end of the cylindrical extension.

13. The spinal implant of claim 12 comprising a polyaxial head connected to the first end of the cylindrical extension; the polyaxial head adapted for connection with the device distinct from the spinal implant.

14. The spinal implant of claim 13 comprising a first transition edge connected to the first converging edge and the straight side and a second transition edge connected to the second converging edge and the straight side.

15. A spinal implant adapted for interconnection with a device distinct from the spinal implant; the spinal implant comprising:

a) a cylindrical extension comprising a first end and a second end opposite the first end; and b) a surgical blade comprising:

i) a slanted side relative to and wider than a diameter of the second end of the cylindrical extension and connected to the second end of the cylindrical extension, wherein the slanted side comprises a first wing positioned on a first side of the cylindrical extension and a second wing positioned on a second side of the cylindrical extension;

ii) a straight side opposite the slanted side; the straight side of a lesser length than the slanted side, wherein a longitudinal axis of the cylindrical extension extends through the straight side;

iii) first and second converging edges connected with the slanted side and converging toward each other as the first and second converging edges approach the straight side; and iv) an aperture proximate the center of the surgical blade; the aperture, positioned between the first and second converging edges, opening to opposed sides of a surgically created space.

16. The spinal implant of claim 15, wherein the surgical blade and the cylindrical extension are uniform.

17. The spinal implant of claim 16, wherein the slanted side intersects with the longitudinal axis of the cylindrical extension at angles other than perpendicular.

18. The spinal implant of claim 17, wherein either the first wing or the second wing is arcuate.

19. The spinal implant of claim 18, comprising a polyaxial head comprising an outer housing and a threaded inward receptacle adapted to receive the device distinct from the spinal implant.

20. The spinal implant of claim 19, comprising a first transition edge connected to the first converging edge and the straight side and a second transition edge connected to the second converging edge and the straight side.

* * * * *